United States Patent [19]

Lobo

[11] Patent Number: 4,507,252

[45] Date of Patent: Mar. 26, 1985

[54] PROCESS FOR THE FORMATION OF DIALKYL PHOSPHOROCHLORIDOTHIONATES

[75] Inventor: Brian J. Lobo, Columbia, Tenn.

[73] Assignee: Stauffer Chemical Company, Westport, Conn.

[21] Appl. No.: 454,824

[22] Filed: Dec. 30, 1982

[51] Int. Cl.$^3$ .............................................. C07F 9/20
[52] U.S. Cl. ................................................. 260/986
[58] Field of Search ....................................... 260/986

[56] References Cited

U.S. PATENT DOCUMENTS 4,322,747  6/1982  Watson, Jr. ...................... 260/986
4,354,983  10/1982  Roszinski et al. .................. 260/986

Primary Examiner—Anton H. Sutto
Attorney, Agent, or Firm—Vivienne T. White

[57] ABSTRACT

Dialkyl phosphorochloridothionates are formed by the chlorination of an alkyl ester of dithiophosphoric acid in a two-stage chlorination reaction. In the first stage, a major portion (e.g., 65% to 95%) of the alkyl ester to be chlorinated is reacted with up to about 95% of the total chlorine to be utilized in the process. The remaining alkyl ester is added to the product from the first stage chlorination reaction and is further chlorinated such that the total chlorine added in the process is about 1 mole per each 0.95 to 1.1 mole of the acid ester utilized in the process.

13 Claims, No Drawings

PROCESS FOR THE FORMATION OF DIALKYL PHOSPHOROCHLORIDOTHIONATES

BACKGROUND OF THE INVENTION

1. Field of the Invention

The present invention relates to a process for the formation of dialkyl phosphorochloridothionates by the reaction of chlorine with an alkyl ester of dithiophosphoric acid.

2. Description of the Prior Art

Various processes for the formation of dialkyl phosphorochloridothionates are known. These compounds are valuable chemical intermediates in the manufacture of such products as pesticides, flotation agents, plasticizers, lubricating oil additives, rubber curing compounds, and flame retardants.

In certain prior art patents a two-stage reaction between the alkyl ester of the acid and chlorine has been proposed. For example, in U.S. Pat. No. 3,897,523 to H. E. Sorstokke, substantially all the acid ester is chlorinated in two chlorination zones with the first zone having from 60-93% of the needed chlorine introduced. A recent improvement to such a process (U.S. Pat. No. 4,332,747 to J. W. Watson, Jr. et al., Col. 3, lines 9-19) contemplates dilution of the chlorine gas reagent after substantially all HCl by-product has been evolved to simplify recovery of the HCl. Another two-stage chlorination procedure in which all the acid ester is present in each of two separate chlorination zones is suggested by U.S. Pat. No. 4,075,292 to K. H. Vopel at Col. 3, lines 38-49. In the Volpe reference the second stage chlorination is accomplished solely by the reaction of $S_2Cl_2$ formed in the first stage chlorination.

It has also been suggested to chlorinate the acid ester in two separate chlorination zones with only a portion of the acid ester being chlorinated in the first of such zones (U.S. Pat. No. 4,078,023 to B. Lippsmeier et al. ). In the Lippsmeier process, a portion of acid ester present in the first stage is subjected to substantially complete chlorination, due to the use of excess chlorine (Col. 3, lines 9-12 of Lippsmeier et al.). After removal of the sulfur precipitate a distillate product from a second stage chlorination is added thereto along with fresh, unreacted acid ester and this mixture is distilled. In a second stage the distillation residue from the first stage is further chlorinated and the sulfur precipitate separated, and the liquid distilled. The distillate product from this stage is recycled to the first stage. The chlorine supplied to both stages is supplied to the acid ester in diluted form.

In the above described process, the unreacted acid ester added to the first stage, after the initial chlorination is completed, can be hazardous due to the thermal instability of unchlorinated material especially during distillation.

U.S. Pat. No. 4,354,983 to Roszinski discloses a process wherein dialkyl dithiophosphoric acid is chlorinated utilizing 3 moles of $Cl_2$ per 2 moles of acid and thereafter a further mole of the acid is added prior to recovering the product by distillation. This process presents the same dangers inherent in the Lippsmeier et al. process.

It is an object of the instant invention to improve the yield of the dialkyl phosphorochloridothionate while decreasing the amount of impurities such as disulfur dichloride produced.

SUMMARY OF THE PRESENT INVENTION

The present invention is a process for the formation of dialkyl phosphorochloridothionates which comprises: (a) reacting a charge of alkyl acid ester of dithiophosphoric acid with chlorine; (b) adding a further amount of the alkyl ester of dithioposphoric acid to the product from (a); and (c) reacting the product from (b) with additional chlorine to complete the chlorination of the dialkyl acid ester.

Surprisingly, in view of the teaching of U.S. Pat. No. 4,078,023, it is not necessary to subject the acid ester to substantially complete chlorination in the first stage chlorination reaction, thereby resulting in a lower level of chlorine consumption than otherwise suggested.

The process of the present invention, unlike the Lippsmaier process, also does not separate sulfur after the first stage chlorination reaction and also does not mix the liquid phase from the first stage chlorination with distilled product from a previous batch.

The present process produces a higher yield of product than achievable by adding chlorine to a single portion of ester, along with a reduced level of undesired sulfur monochloride by-product and a reduced level of high boiling impurities in the final product. The addition of unchlorinated alkyl acid ester to the alkyl ester which had been chlorinated results in a reaction of the added alkyl acid ester with undesired sulfur chlorides (e.g., disulfur dichloride) yielding the more desirable di-(O,O-dialkyl-thionophosphoryl) disulfides. These disulfides are then converted to the desired endproduct by the chlorine added during the second stage chlorination reaction.

DETAILED DESCRIPTION OF THE INVENTION

The present process is applicable to the chlorination of alkyl esters of dithiophosphoric acid (alkyl acid esters or alkyl esters) having the formula

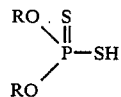

where R is independently an alkyl radical of 1 to 8 carbon atoms or a cycloalkyl radical of 5 or 6 carbon atoms.

In the practice of the invention chlorine in an amount of from about 0.85 mole to about 1 mole of chlorine and preferably from about 0.9 mole to about 0.95 mole is reacted with from about 0.95 to about 1.1 moles of the alkyl ester.

The first stage chlorination comprises reacting a major amount, e.g., from about 65% to about 95% by weight, of the total amount to be reacted, of the alkyl ester with chlorine. The chlorine is generally reacted in a molar ratio of from about 0.85:0.9 to about 0.95:1, based on the amount of acid ester to be chlorinated in the first stage. The chlorination takes place at a temperature of from about 10° C. to about 80° C. and desirably from about 40° to about 60° C., preferably using undiluted chlorine.

The reaction of the acid ester with chlorine is thought to proceed as follows with a small amount of disulfur dichloride ($S_2Cl_2$) by-product being generated in Stage I.

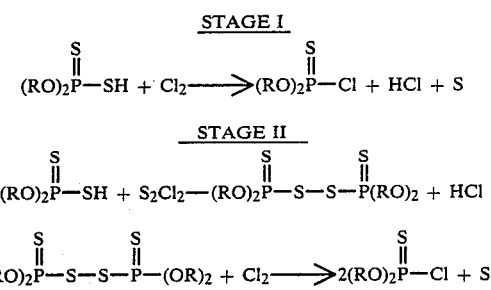

STAGE I $$(RO)_2\overset{S}{\underset{\|}{P}}-SH + Cl_2 \longrightarrow (RO)_2\overset{S}{\underset{\|}{P}}-Cl + HCl + S$$

STAGE II $$(RO)_2\overset{S}{\underset{\|}{P}}-SH + S_2Cl_2 \longrightarrow (RO)_2\overset{S}{\underset{\|}{P}}-S-S-\overset{S}{\underset{\|}{P}}(RO)_2 + HCl$$

$$(RO)_2\overset{S}{\underset{\|}{P}}-S-S-\overset{S}{\underset{\|}{P}}-(OR)_2 + Cl_2 \longrightarrow 2(RO)_2\overset{S}{\underset{\|}{P}}-Cl + S_2$$

After completion of this first stage chlorination a further portion of the acid ester, generally from about 0.05 to about 0.2 mole, is added to the reaction product from the first stage chlorination reaction, and chlorination is begun in a second stage procedure so as to give an overall chlorine addition of from about 0.85 to about 1 mole per 0.95 to 1.1 mole of the acid ester. The chlorination is allowed to proceed at the treating temperatures described above until the process is completed.

Preferably, from about 0.90 mole to about 0.95 mole of chlorine is reacted with from about 0.9 mole to about 1 mole of the acid ester in the first chlorination stage and thereafter a further 0.05 to about 0.1 mole of chlorine is reacted with a further 0.1 mole of the alkyl ester.

The foregoing invention is further illustrated by the Examples which follow.

EXAMPLES 1–3

The following Examples (Nos. 2 and 3) illustrate the process of the present invention with Example 1 being presented for comparative purposes only to illustrate a prior art technique involving a single stage chlorination procedure.

Three chlorination reactions were performed using the same sample of the dimethyl ester of dithiophosphoric acid (DTA). The first chlorination was a control run in which 0.95 moles of chlorine was added to the entire 1 mole sample of DTA to produce a 95% level of chlorination (Example 1). In the remaining two runs (Examples 2 and 3), the DTA to be chlorinated was split into two portions with 90% of the starting sample, 0.9 mole being treated with 0.765 moles of chlorine until it was chlorinated to the 85% level. The remaining 10% balance or 0.1 mole of DTA was then added, and chlorination with 0.185 mole of chlorine was resumed to raise the chlorination level to 95%. The total time for chlorination in each run was 1 hour at 55° C. The amount of $S_2Cl_2$ and di-(O,O-dimethyl-thionophosphoryl) disulfide was determined at this point. The reaction mixture for each run was then held at 60° C. for 45 minutes during which any color change was noted and the $S_2Cl_2$ and disulfide levels were again determined. The mixture was then distilled until the pot temperature reached 80° C. at 2 mm. Hg. The $S_2Cl_2$ level and yield of desired endproduct had been determined in the crude mixture prior to the distillation procedure. The vapor temperature of the distillate was measured during distillation. The following results were obtained:

| Example No. | After Chlorination % $S_2Cl_2$ | % Disulf. | Time to Color Change (Mins.) |
|---|---|---|---|
| 1* | 9.97 | 2.4 | 14.5 |
| 2 | 9.69 | 2.0 | 44 |
| 3 | 9.01 | 2.5 | 37.5 |

| Example No. | After 45 min. Hold % $S_2Cl_2$ | % Disulf. | % $S_2Cl_2$ in Crude |
|---|---|---|---|
| 1* | 5.25 | 1.1 | 2.3 |
| 2 | 5.37 | 1.0 | 1.6 |
| 3 | 5.18 | 1.4 | 1.1 |

| Example No. | Crude Yield % | Crude Yield (%)-Corr. for $S_2Cl_2$— | Final Vapor Temp. (°C.) |
|---|---|---|---|
| 1* | 72.1 | 70.4 | 50 |
| 2 | 74.8 | 73.6 | 38 |
| 3 | 73.4 | 72.6 | 37 |

*Control - not part of the present invention.

An increased time for the chlorinated material to change color (i.e., better color stability), a lowered level of $S_2Cl_2$ impurity, a lower vapor temperature for the distilled distilled material (i.e. lower level of undesired high boiling by-product), and an increased yield of the desired, crude endproduct (before distillation) were noted for the split chlorinations of Examples 2 and 3 as compared to the single step chlorination of Example 1.

The foregoing Examples illustrate certain preferred embodiments of the present invention and should not therefore be construed in a limiting sense. The scope of protection sought is set forth in the claims which follow.

What is claimed:

1. A process for the formation of dialkyl phosphorochloridothionates by chlorinating an alkyl ester of dithiophosphoric acid which comprises:
   (a) reacting a charge of an alkyl ester of dithiophosphoric acid with chlorine to form a reaction product containing disulfur dichloride;
   (b) reacting an additional amount of the alkyl ester of dithiophosphoric acid with the disulphur dichloride contained in the reaction product of (a); and
   (c) further chlorinating the product of (b) with a reactant consisting essentially of chlorine to complete the chlorination process.

2. A process as claimed in claim 1 wherein the amount of ester chlorinated in (a) is from 65% to 95% by weight of the total amount of the ester to be reacted in the process.

3. The process as claimed in claim 1 wherein the amount of ester charged in (b) is from 5% to 35% by weight of the total amount of the ester to be reacted in the process.

4. The process as claimed in claim 1 wherein from about 0.9 to about 1 mole of the acid is charged in (a).

5. The process as claimed in claim 1 wherein from about 0.85 to about 0.95 mole of chlorine is reacted with the acid in (a).

6. The process as claimed in claim 1 wherein from about 0.05 to about 0.2 mole of the dithiophosphoric acid ester is charged in (b).

7. The process as claimed in claim 1 wherein from about 0.05 to 0.1 mole of chlorine is reacted in (c).

8. The process as claimed in claim 1 wherein the chlorination takes place at from about 10° to about 80° C.

9. The process as claimed in claim 1 wherein the chlorination takes place at from about 40° C. to about 60° C.

10. A process for the formation of dialkyl phosphorochloridothionates by chlorinating an alkyl ester of dithiophosphoric acid comprising: (a) reacting from about 0.85 to 0.95 moles of chlorine with from 0.9 to 1 mole of the dithiophosphoric acid ester to form a reaction product containing disulfur dichloride; (b) reacting the disulfur dichloride contained in the reaction product of (a) with a further charge of from 0.05 to about 0.2 moles of dithiophosphoric acid ester; and (c) adding from about 0.05 to about 0.1 mole of a reactant consisting of essentially of additional chlorine to the product of (b) to complete the chlorination process.

11. The process as claimed in claim 1 wherein from about 0.90 to about 0.95 moles of chlorine is charged in (a).

12. The process as claimed in claim 10 wherein the chlorination takes place at from about 10° C. to about 80° C.

13. The process as claimed in claim 10 wherein the chlorination takes place at from about 40° C. to about 60° C.

* * * * *

UNITED STATES PATENT AND TRADEMARK OFFICE
CERTIFICATE OF CORRECTION

PATENT NO. : 4,507,252
DATED : March 26, 1985
INVENTOR(S) : Brian J. Lobo

It is certified that error appears in the above—identified patent and that said Letters Patent is hereby corrected as shown below:

Under "U.S. PATENT DOCUMENTS" on the face of the patent, please insert before "4,322,747" the following:

| | | | |
|---|---|---|---|
| 3,089,890 | 5/1963 | Chupp et al. | 260/986 |
| 3,897,523 | 7/1975 | Sorstokke | 260/986 |
| 4,075,292 | 2/1978 | Vopel et al. | 260/986 |
| 4,078,023 | 3/1978 | Lippsmeier et al. | 260/986 |

Col. 1, line 33, "Volpe" should be -- Vopel --.
Col. 2, line 8, "dithioposphoric" should be -- dithiophosphoric --.
Col. 2, line 9, ";" should be deleted.
Col. 2, lines 16-17, "Lippsmaier" should be -- Lippsmeier --.
Col. 4, line 20, delete one "distilled".
Col. 5, line 8, after "consisting" delete -- of --.

Signed and Sealed this

Twenty-ninth Day of April 1986

[SEAL]

Attest:

DONALD J. QUIGG

Attesting Officer

Commissioner of Patents and Trademarks